US008814356B2

(12) United States Patent
Ehrmann et al.

(10) Patent No.: US 8,814,356 B2
(45) Date of Patent: Aug. 26, 2014

(54) PHYSICAL MODEL EYE SYSTEMS AND METHODS

(75) Inventors: Klaus Ehrmann, Manly (AU); Ravi Chandra Bakaraju, Eastlakes (AU); Darrin Falk, Stanmore (AU)

(73) Assignee: Brien Holden Vision Institute, Sydney NSW (AU)

( * ) Notice: Subject to any disclaimer, the term of this patent is extended or adjusted under 35 U.S.C. 154(b) by 423 days.

(21) Appl. No.: 12/999,467

(22) PCT Filed: Jun. 17, 2009

(86) PCT No.: PCT/AU2009/000791
§ 371 (c)(1),
(2), (4) Date: Dec. 16, 2010

(87) PCT Pub. No.: WO2009/152582
PCT Pub. Date: Dec. 23, 2009

(65) Prior Publication Data
US 2011/0170059 A1    Jul. 14, 2011

(30) Foreign Application Priority Data

Jun. 17, 2008 (AU) ................................ 2008903071

(51) Int. Cl.
A61B 3/00      (2006.01)
A61B 3/10      (2006.01)
G09B 23/22     (2006.01)
G09B 23/34     (2006.01)

(52) U.S. Cl.
CPC .............. G09B 23/22 (2013.01); G09B 23/34 (2013.01)
USPC .......................................... 351/205; 351/200

(58) Field of Classification Search
USPC ......... 351/200, 205, 208–212, 216, 220, 222, 351/236, 243
See application file for complete search history.

(56) References Cited

U.S. PATENT DOCUMENTS

| 1,042,815 A | 10/1912 | Myers |
| 1,630,944 A | 10/1925 | Ingersoll |
| 2,068,950 A | 2/1935 | Hamilton |
| 5,532,770 A | 7/1996 | Schneider et al. |

(Continued)

FOREIGN PATENT DOCUMENTS

| DE | 10341161 B3 | 2/2005 |
| EP | 0940118 | 9/1999 |

OTHER PUBLICATIONS

PCT International Search Report.
Written Opinion of the International Searching Authority.

(Continued)

*Primary Examiner* — Joseph P Martinez
*Assistant Examiner* — Brandi Thomas
(74) *Attorney, Agent, or Firm* — Smith Moore Leatherwood LLP; David M. Krasnow (57) ABSTRACT

An optically realistic model eye is described. The optically realistic eye model has an optical axis and includes: an anterior replaceable module comprising a model cornea, model iris and model lens rotatably mounted for rotation about said axis, said module being representative of an emmetropic or pathological natural eye; an enclosure located posterior to said module and adapted to enclose a retinal area within which an image of an external object is brought to focus by said module; and a photoactive device movable within said enclosure and retinal area and adapted to detect or reflect a portion of the image for inspection, processing or analysis.

22 Claims, 5 Drawing Sheets

(56) References Cited

U.S. PATENT DOCUMENTS

| | | |
|---|---|---|
| 5,652,640 A | 7/1997 | Schneider et al. |
| 5,875,017 A | 2/1999 | Ohnuma et al. |
| 6,485,142 B1 | 11/2002 | Sheehy et al. |
| 6,626,535 B2 | 9/2003 | Altmann |
| 7,036,933 B2 | 5/2006 | Yamaguchi et al. |
| 7,066,598 B2 | 6/2006 | Niven |
| 2002/0085172 A1 | 7/2002 | Altmann |
| 2007/0110285 A1* | 5/2007 | Hanna et al. .................. 382/117 |
| 2008/0015553 A1* | 1/2008 | Zacharias ........................ 606/4 |
| 2010/0185260 A1* | 7/2010 | Olson ............................. 607/54 |

OTHER PUBLICATIONS

Extended European Search Report received on Dec. 16, 2013 in PCT/AU2009/000791 (8 pages).
Patent Examination Report No. 1 mailed on Mar. 17, 2014 in Australian Patent Application No. 2009260126 (3 pages).

* cited by examiner

PHYSICAL MODEL EYE SYSTEMS AND METHODS

CROSS-REFERENCE TO RELATED APPLICATIONS

This application is a national stage application under 35 U.S.C. 371 of International Application No. PCT/AU2009/000791 filed 17 Jun. 2009, which claims priority to Australian Application No. AU 2008903071 filed 17 Jun. 2008, the disclosures of which are expressly incorporated herein by reference.

FIELD OF THE INVENTION

This invention relates to physical model eyes, model eye systems and to methods of their use. The model eyes, systems and methods can be used to evaluate corneal re-shaping and corrective lenses (such as contact, spectacle and intraocular lenses—or IOLs), as well as to calibrate ophthalmic instruments, or to simulate functions, defects, pathologies, surgical modification and/or injuries of the natural eye.

BACKGROUND OF THE INVENTION

It is desirable that the physical model eye is realistic in that it is substantially life-size having a realistic cornea, iris, lens and focal distance, and a similar field of view to a natural eye.

While such schematic model eyes are able to simulate the optical characteristics of the eye mathematically, they are not useful for assessing the performance of real corrective lenses IOLs (intraocular lenses) in combination with the eye.

Some physical model eyes of the prior art are intended to demonstrate basic eye functions to groups of students and are therefore greatly enlarged, simplified and not optically realistic. Examples are U.S. Pat. No. 1,042,815 [Myers 1912], U.S. Pat. No. 1,630,944 [Ingersoll, 1927] and U.S. Pat. No. 2,068,950 [Hamilton, 1937]. Such physical models are neither optically nor anatomically accurate and are therefore quite unsuited for the realistic evaluation of pathologies, treatments or corrective lenses.

Known physical model eyes of more relevance are those that attempt to accurately simulate selected optical and physical characteristics of the natural eye in order to test real eyewear or to calibrate ophthalmological instruments.

U.S. Pat. Nos. 5,532,770 and 5,652,640 [Schneider 1996] disclose a horizontally-mounted model eye system for evaluating IOLs, the system having a cornea, a liquid-filled posterior chamber containing the IOL, a fovea window located near the fovea and a fovea projector (a telescopic optical instrument) located behind the fovea window to allow a person to inspect the image at the fovea window. The chamber has a flexible bladder-like joint that allows the fovea projector to be moved axially relative to the IOL while retaining the liquid in the chamber. Off-axis portions of the retinal image are not of interest and no provision is made for their visualization.

U.S. Pat. No. 5,875,017 [Ohnuma et al 1997] discloses a lens system for evaluating a test IOL or contact lens that employs a CCD camera sensor located to capture the fovea image. While the test IOL or contact lens can be realistic and an accurate anterior cornea surface can be provided to support the test contact lens, the lens system is not realistic as it depends on a wide-angle camera-type objective lens placed in front of the system to bring an image to focus over the flat area of the CCD camera sensor.

U.S. Pat. No. 6,485,142 [Sheehy, 2002] discloses a horizontally-mounted, two-chamber, spherical, liquid-filled model eye that is about 6.5 times the size of a natural eye and has lenses to simulate the natural cornea and lens. It is used to evaluate protective filters and eyewear located between a radiation source and the model eye. The posterior spherical surface of the model eye, representing the retina, is translucent (frosted) and a radiation sensor (such as a CCD camera) is located outside the eye where it can detect the radiation intensity of a portion of the image formed on the frosted retina. For this purpose, the sensor can be moved concentric with the retina surface in the horizontal plane so that the radiation intensity at different angles can be examined.

U.S. Pat. No. 6,626,535 [Altmann 2003] et al discloses a single-chamber, liquid-filled and vertically-mounted model eye for testing real contact lenses. In one embodiment, the cornea and eye lens are jointly simulated by a solid optical element having an anterior surface machined to the shape of a natural cornea and having a posterior surface that forms the anterior end of the posterior chamber. A contact lens can be placed on the model cornea in a centered or decentered manner, as desired. The retina is simulated by a transparent or reflective concave surface that forms the posterior end of the chamber. A flexible bladder-like joint allows the retina surface to be moved to change eye-length or to vary centration of the retina surface while retaining the liquid in the chamber. Whilst the use of a pinhole-like fovea window is disclosed, evaluation of the test contact lens is performed by refractometer or wavefront instruments located in front of the eye that rely upon reflection from the model retinal surface. However, the incident angles at which such instruments can be used effectively, are severely limited.

U.S. Pat. No. 7,036,933 [Yamaguchi, 2006] discloses a horizontally-mounted tubular model eye for use in calibrating wavefront measuring instruments used on natural eyes. It is not physically realistic in shape or in the contours of the optical surfaces. An anterior lens simulates both the natural cornea and lens and a posterior diffusion surface is located at the focal point of the lens to simulate the fundus of the retina. A phase plate is inserted between the lens and the diffusion surface to correct for aberrations introduced by the lens or to add controlled aberration to the model eye. An interferometric calibration method using the model eye is also disclosed.

U.S. Pat. No. 7,066,598 [Niven 2006] discloses a vertically-mounted two-chamber model eye capable of accommodating separate liquids representing both humors. The model cornea appears to have a realistic posterior surface as well as a realistic anterior surface, the natural lens is represented by a solid machined lens, the iris is simulated by an aperture ring located in front of the lens and is used to mount the lens within the posterior chamber, and the retina is simulated by the flat inner surface of an end cap that seals the posterior chamber of the model eye and is located at a fixed distance from the lens. A feature of this model is the provision of gaps between the iris ring and the lens to permit air trapped in the posterior chamber to gravitate upward into the anterior chamber. The model eye is used with refractometers or the like in the same manner as that of Altmann and also can be used for refractometer calibration.

It will be understood that any reference herein to prior art does not constitute an admission as to the common general knowledge of a person skilled in the art.

BRIEF SUMMARY OF THE INVENTION

From one aspect, the physical model eyes, systems and methods of the present invention are characterized by the use of a photoactive device that is moveable both laterally and axially within the retinal area where images are brought to focus to detect and/or reflect a portion of an image for inspection, evaluation, processing or analysis. The device is preferably small so that it can be moved widely within a spherical-form retinal area. It may be a photodetector array (including, if desired, a bundle of optical fibers terminating in the retinal area and optically coupled to a photodetector array outside the retinal area), or a reflector surface. It may also include a photoemitter such as a point-source light for use in determining the single-pass characteristics of the anterior components of the model eye. Actuator means is preferably provided to support and move the device from position to position within the retinal area and, at each position, is preferably able to reciprocate the device to and/or fro through a plurality of locations to allow the location of best image focus to be determined. [Best image focus or 'best-focus' is herein used to mean least cylinder power or the circle of least confusion.]

The model eyes of this invention are preferably optically realistic in that they at least optically function in a similar fashion to that of the natural eye. In this regard, they preferably have optically realistic lenses, corneas and irises, which give rise to a realistic field of view and focal distance. They may also have an optical resolution which is similar to that of the natural eye. In scale, they may also be substantially life-size. However, a model retinal surface is not present so that the photoactive device can be moved to, through or along any location in the retinal area where it is expected that an image will be brought to focus, or it can be moved to, through or along the known contour of any particular retina of interest, the coordinates of which being used by the actuator means to position device. [Since a variety of different focal fields and retinal contours may be of interest, they can be regarded as collectively occupying three-dimensional 'virtual' retinal contour or envelope, which is herein simply referred to as the 'retinal area', the term 'retinal contour' being reserved for the shape of a particular retina, unless otherwise indicated.]

The actuator means is preferably controlled by computer having controller means for driving the actuator means to position and/or reciprocating the device as desired or programmed by the user. The device is preferably a photodetector having a two-dimensional array of photo-sensors, the output of which is preferably connected to image processing means within the computer and the processed image output so generated is preferably stored in computer memory means. It is then convenient to also store reference retinal contours in the memory and use their coordinates to position the device, as desired. The image processor means is preferably adapted to accept the output of the photodetector at each location during reciprocation and to compare or otherwise process these outputs to determine the location of best image focus at the position of the device within the retinal area. In addition, the image processor means is preferably adapted to derive a curvature of field plot within the retinal area from the locations of best-focus for a series of device positions and to store the plot data within the memory for subsequent display, analysis or other use.

While the size of the retinal area of interest will depend upon the use of the particular model eye or system, it is such that it can always be probed by axial, lateral and/or circumferential movement of the photoactive device therein. For example, the retinal area can be a short portion of the optical axis near the expected location of the fovea, a substantially planar arc extending laterally and curving forward from the axis at or near the fovea, or a three-dimensional cup-like shell of approximate spherical form. Any one of these retinal areas can intersect or contain portions of multiple specific retinal contours or shapes derived from measurements on natural eyes, from theoretical considerations, or from hypothetical speculations. Thus, the model eyes, systems and methods of the invention enable the curvature of field (locus of best-focus) for any combination of model cornea, model iris, model lens, test IOL or external corrective lens to be determined over a wide range of peripheral angles for a variety of test objects within the field of view. They also enable the defocus along any predetermined retinal contour of interest to be visualized, measured or recorded. These important capabilities are not present in model eyes, systems and methods of the prior art known to the applicants.

More particularly, where it is desired to plot the curvature of field generated by a particular combination of optical elements, the photoactive device can be moved to any position in the retinal area and then reciprocated through the image through best-focus. By repeating this procedure at a plurality of positions in the retinal area, the curvature of field of the model eye can be readily determined for a particular test image or for a series of different test images. [A test image here means an image of an external test object or objects—near and/or distant—within the field of view of the model eye, an example being a normal eye chart or a projected light pattern used by optometrists.] Additionally, or alternatively, the device can be placed at successive positions along a predetermined retinal contour of interest to allow variation of image focus along the contour to be visualized, measured and/or recorded. Since such curvature of field and focus plots can cover large peripheral angles, the model eyes, systems and methods of this invention are particularly suited to the investigation of progressive myopia and the evaluation of anti-myopia lenses such as those taught by Smith et al in U.S. Pat. No. 7,025,460, and corneal modifications. They will also be of value in assessing the performance of multi or mono-focal spectacle, contact and IOL lenses, as well as modified corneas, even where acuity of central vision is of prime or sole interest. [Investigation of the effects of modified or molded corneal surfaces depends upon the use of model corneas configured to the contour desired by or resulting from the molding procedure—such as, laser ablation, autokeratology or the use of onlays or inlays.] The model eyes, systems and methods of this invention are also of value in the investigation of pathologies or abnormalities of the natural eye related to misshapen lenses, corneas or retinas.

As noted above, it is desirable to use a device that has a small photoactive area relative to the area of the retina of a human eye, preferably less than 10%. Most preferably, the photoactive area of the device approximates that of the fovea of the natural eye (about 2 mm in diameter). However, devices having photoactive areas between 1-4 mm across are generally satisfactory. Another consideration in anti-myopia investigations is that the size of the photoactive device should preferably be small relative to the length of the arcuate path along which it can be moved, which path normally extends to an angle of at least 30° from the axis. This tends to reduce cost and mechanical complication and to improve accuracy. Again, it is preferred that the length of the device is less than 30% of the maximum path length, preferably less than 15% and, most preferably, less than 10% thereof. Of course, where interest is confined to central vision and on-axis images, little angular or off-axis movement of the device is required and a photoactive area approximating that of the fovea will be satisfactory.

We have found that the photoactive device of most value is a small-area CCD or CMOS color-sensitive photodetector array of the type used in digital cameras. The use of an array capable of sensing color, offers important advantages as it allows capture of additional image data during the through-focus movement, such as that indicative of chromatic and other image aberration. This data is of value in assessing aberrations of the model eye with and without the use of corrective lenses or simulated retinal molding procedures. In fact, when such movable detectors—polychromatic or not—are used with an external point light source, higher order—as well as lower order—aberrations can be computed from the data generated. As already noted, lower order aberrations such as defocus, spherical aberration and cylinder power are also available from the data generated by using a photodetector device with focused images. For convenience and economy, the array is preferably flat and not curved to match the curvature of a natural retina, any resulting errors being negligible for a small area array. Errors resulting from the use of larger planar arrays can be reduced by use of through-focus reciprocation as indicated above. In any case, however, it is preferable to ensure that the array faces the posterior of the lens, a nodal point of the model eye or the center of retinal curvature in all positions.

Besides preferably approximating the size of the fovea of a human eye, the photodetector array preferably has a resolution (of in terms of pixel density) that approximates—as far as practicable—the rod density in the fovea of the eye, which equates to a pixel size of about 1-1.5μ, but pixel sizes much larger than this will be useful nevertheless. Though 'single-pixel' devices may be used, they tend to be difficult or laborious to use if the pixel size is small and to lack resolution if it is large. The image signals output from a two-dimensional array can provide much more information in a given period of time, which can be processed, analyzed and stored using conventional image processing techniques so that curvature of field can be quickly determined and image quality, defocus and cylinder power at any location on any retinal contour of interest can be readily displayed, recorded and analyzed by the processor means using conventional software. Such a photodetector device also can be used to detect and analyze stray light elsewhere in the back of the model eye. Finally, the photodetector device may comprise a bundle of optical fibers that extends into the retinal area and that is connected to photosensor (such a photodetector array) that is physically displaced from the retinal area.

However, the photoactive device can also be or include a reflective surface that may be positioned to reflect portion of a test image projected into the model eye for evaluation by a conventional refractometric or wavefront instrument positioned in front of the model eye. Finally, as already noted, the photoactive device may include a point-source photoemitter capable of illuminating the back of the model lens from anywhere on a retinal contour, thereby providing a unique method of investigating the single-pass wavefront characteristics of the front-end of the model eye using a wavefront analyzer located in front of the model eye or system. The light source can be an LED, laser diode or fiber optic tip with a suitable pinhole aperture, if needed. Finally, the device may include in combination a photodetector array, a reflector and/or a light source compactly arranged at known distances from one another so that any one may be selected and positioned accurately in the retinal area.

While it is desirable that the 'front-end' of the model eye includes an optically realistic cornea, iris and lens (or test IOL), the 'back-end' of the model eye preferably does not comprise a physically accurate posterior chamber or any conventional retinal surface. Instead, the moveable photoactive device is preferably located within a light-proof posterior enclosure so that it can be moved as desired within the retinal area. Preferably, the posterior enclosure can hold liquid that simulates the optical dispersion of the vitreous body of the natural eye. When such a liquid is used, the device is effectively immersed and moved within it. The enclosure can be smaller than the retinal area of interest if its wall or walls are sufficiently flexible or elastic to permit the device to be moved as desired within that area. Or, the perimeter of the enclosure can be rigid and large enough to (i) encompass the entire retinal area of interest, (ii) allow full movement of the device therein, and (iii) accommodate means for supporting and moving the device. Preferably, however, the enclosure is simply a flexible bladder with the device sealed in its posterior end so that it will be immersed within any liquid in the posterior enclosure and so that input/output wires or optical fibers from the device are easily accessible outside the enclosure.

As noted above, the photoactive device is preferably supported and moved by processor-controlled actuator means. In one form this can be a universal-type robotic-arm capable of positioning the device accurately anywhere of interest within or around the retinal area or, indeed, within the posterior chamber or enclosure. The robotic arm may also be controlled to face the device at a nodal point of the model eye, or at the center of retinal curvature, from any position and should be capable of holding it steady in position for extended periods of time. Such actuator means is preferably also controllable to execute the reciprocatory movement for through-focusing at each position in the retinal area, when needed. While the entire retinal area of interest can be covered in this way—along with most of the interior of the enclosure—such a universal-type robotic arm is likely to be expensive.

More economical actuator means can be provided in accordance with another aspect of this invention by limiting the range of movement of the device. For example, where only on-axis through-focus near the fovea is of interest, the device can be mounted on a support arm that incorporates an axially aligned linear actuator. Where arcuate movement of the device within a plane (usually including the axis) in conjunction with through-focus is adequate, the support arm can be mounted on an rotary actuator having an axis of rotation arranged to pass through the optical axis, the lens, a nodal point or the center of curvature of the notional retina of the model eye. And, where a non-rotationally symmetric retinal contour is of interest, it can be readily simulated using the planar arcuate configuration indicated above and a succession of sectional retinal contours correspond to a succession of meridia. Asymmetry in correctional lenses or their orientation with respect to the optical axis, or asymmetry in the front-end optics of the model eye, can also be handled with the planar arcuate configuration by providing for rotation of a front-end module of the model eye about the optic axis relative to the posterior of the model eye. Of course, if it can be assumed that a retinal contour of interest is rotationally symmetric (but not necessarily spherical) about the optical axis, only one sectional quadrant of the three-dimensional retinal contour of interest will be needed and a retinal area comprising a single arcuate planar quadrant will normally suffice.

It is desirable that the front end modules used in the model eyes and systems of this invention are optically realistic in that their key dimensions and optical characteristics approximate those of the natural eye as closely as practicable so that realistic corrective modalities can be tested. For example, it is desirable that the shape of the anterior cornea surface be accurately reproduced so that it will take production contact lenses. The posterior surface of the cornea may also be accurately reproduced along with a simulated iris and model lens. However, it is desirable that the lens be replaceable with a test IOL. Such a front-end module will have a separate anterior chamber that can be filled with liquid representative of the aqueous humor, or it can be formed to share the liquid of the posterior chamber, when that liquid is used.

From another aspect, the invention relates to a model eye model eye system which is optically representative of a natural eye and is suitable for testing contact, spectacle and intraocular lenses or simulating natural corneas that have been reshaped by various techniques. The model eye preferably has a front-end module mounting the model cornea, iris and lens with appropriate spacing on a common optical axis, as well as a posterior enclosure that at least partially encloses a retinal area within which optical images formed by the model eye can be brought to focus, the model eye including a photoactive device moveable within the retinal area to detect or reflect at least portion of an image formed therein for inspection, analysis or storage. Preferably, the front-end module is rotatable with respect to the posterior enclosure about the optical axis.

From another aspect, the invention involves methods that generate an image of a test object within the retinal area of a model eye or system and move a photoactive device from position to a position within the retinal area to detect or reflect portion of the image at each position for inspection, evaluation, processing or analysis. The methods may additionally involve moving or reciprocating the device, preferably to and/or from a nodal point of the model eye, at each position and processing the resultant variation of the image portion to determine the location of best-focus for that position. The method may also include, deriving the coordinates of a retinal contour from computer memory, controlling the actuator means to move the device to a position having those coordinates, and observing or recording the defocus, if any, of the image portion at that position. The methods may also include using actuator means to support and move the device and, preferably, using a rotary actuator to rotate the device, using a linear actuator that is rotated with the device to reciprocate the device to-and-fro, and processing the image portions thereby generated to determine the location of best-focus for each position of the device within the retinal area. Also, the above methods may additionally involve the step of incrementally rotating a front-end optical module of a model eye or system and repeating one or more of the above steps for each increment.

BRIEF DESCRIPTION OF THE DRAWINGS

FIG. 2a shows a model eye fitted with a contact lens and shows a spherical form shell-like retinal area containing multiple retinal contours, while FIGS. 2b-2e indicate some different forms of retinal areas and different ways in which the photoactive device can be moved.

DESCRIPTION OF EMBODIMENTS

Figure 1:
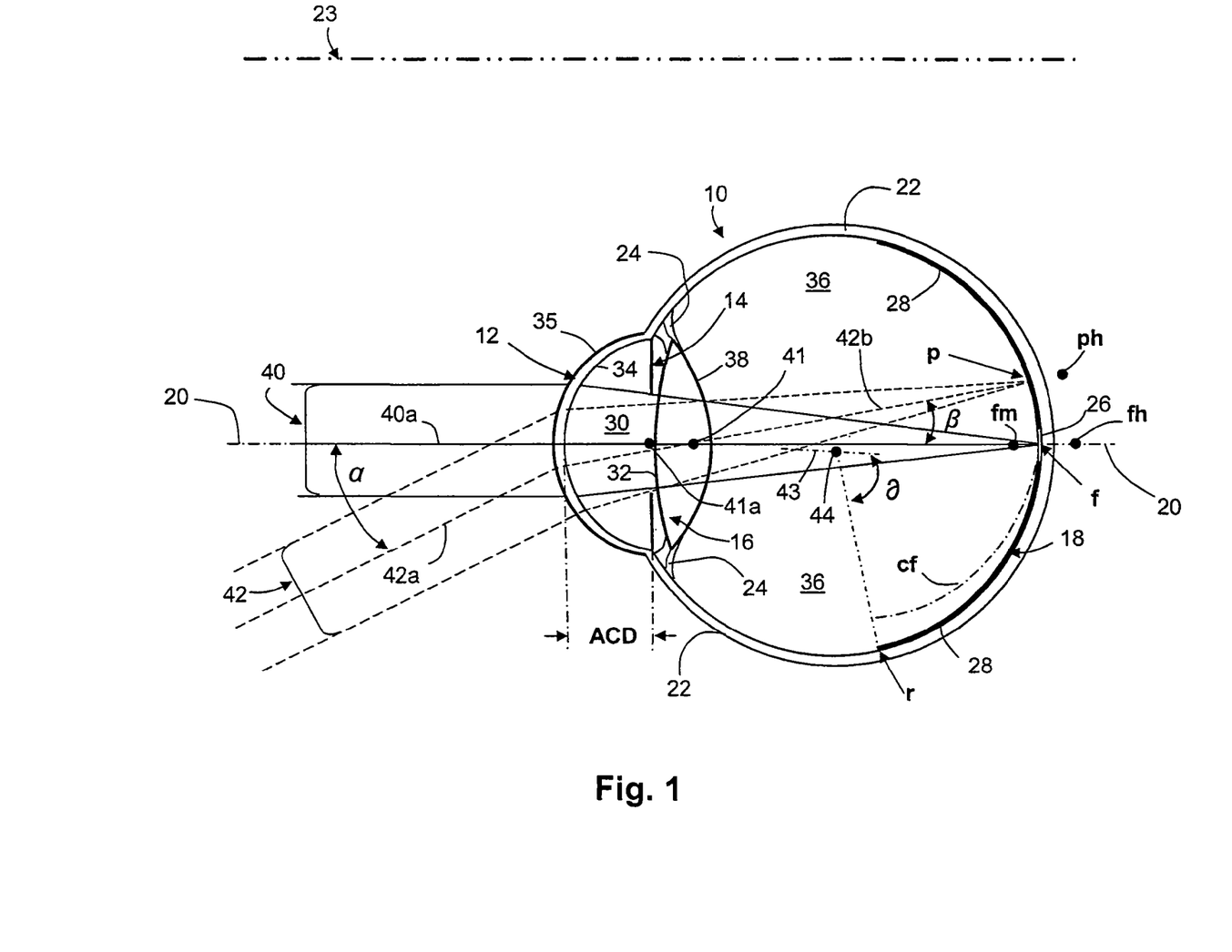
FIG. 1 is a diagrammatic sagittal sectional plan of a human eye showing axial and off-axis incident beams.

FIG. 1 is an idealized diagrammatic sectional plan of a left human eye 10 having a cornea 12, iris 14, lens 16, retina 18 and optic axis 20, the wall or sclera of the globe of eye 10 being indicated at 22 and the midline between the two eyes of a person being indicated at 23. Retina 18 lines the inside of the back (posterior) of eye 10 and lens 16 is supported by zonules (suspensory ligaments) 24 from sclera 22. Retina 18 includes a small central portion 26 comprising the fundus or fovea and a large peripheral area 28 (indicated by a heavy line). The anterior chamber 30 of the eye lies between the anterior (front) surface 32 of lens 16 and the posterior (rear) surface 34 of cornea 12, iris 14 being located in the anterior chamber 30, which is filled with the transparent aqueous humor (not identified) of the eye. The anterior chamber depth—ACD—is generally taken to be the axial distance between the posterior surface 34 of cornea 12 and the plane of iris 14. The posterior chamber 36 of eye 10 is bounded at the rear by retina 18, by the posterior surface 38 of lens 16 and zondules 24 at the front and, in between retina 18 and lens 16, by sclera 22. It is filled with the transparent vitreous body or humor (not identified) of the eye.

In an ideal or emmetropic eye with a straight-ahead on-axis gaze directed at distance, a central or paraxial beam 40 from a distant object will be brought to focus at point f on-axis at the fovea in the middle of central portion 26 of retina 18 to provide ideal visual acuity. At the same time, a peripheral or off-axis beam 42 from a distant object will be brought to focus at point p in the periphery 28 of retina 18. When the gaze is directed at a near on-axis object, lens 16 accommodates by changing shape (and optical power) to bring near on-axis objects to focus at point f and near off-axis objects to focus at point p in peripheral retina 28. This ideal is not achieved in many eyes. While myopes (the 'short-sighted') usually can bring near on-axis objects to focus at f, their accommodation is unable to bring distant on-axis objects to focus at f and, instead, such objects are focused in front of central retina— say, at point fm. Hyperopes (the 'long-sighted') have the reverse problem in that near on-axis objects are focused behind central retina 26—say, at point fh. It is generally agreed that these faults are caused in large part by distorted retinal shape; specifically, by excessive elongation (eye length) in myopes and insufficient elongation (eye length) in hyperopes. In presbyopes, however, the retinal area may have an optimal contour but lens accommodation is insufficient to bring axial near images to focus on the fovea, such images being focused behind the retina (say, also at point fh). Smith et al showed that focal errors in the periphery are important in stimulating axial elongation of retinal contour (eye-lengthening) in myopia as well as axial shortening of retinal contour in hyperopia. Specifically, the retinal contours of myopes who are hyperopic in the periphery tend to grow more axially relative to the rest of the eye while the retinal contours of hyperopes who are myopic in the periphery tend to grow relatively less axially. Smith et al therefore suggested the use of corrective lenses which will generate a curvature of focal field, indicated by dash-dot line cf (only shown in the temporal quadrant of peripheral retina 26 for clarity). Thus, there is a need for a model eye which will readily and accurately simulate the various abnormal retinal shapes of myopic and hyperopic patients and be capable of determining the corrective curvatures of peripheral focal field imposed by 'anti-myopia' corrective lenses. In addition, there is need for a model eye capable of simulating presbyopia, which is common in people over about 45 years old. These capabilities are beyond those of the prior-art physical model eyes known to the applicants.

In FIG. 1, the focal errors at points fm, fh and ph together with curvature of field cf have been greatly exaggerated and the paths of paraxial and peripheral beams 40 and 42 have been greatly simplified as refractions at the interfaces 32 and 38 of lens 16 are not shown, but FIG. 1 shows that (i) the incident peripheral angle α which central ray 42a of off-axis beam 42 makes with optic axis 20 is not the same as the peripheral angle β of central ray 42b inside the eye, and that (ii) notionally, both peripheral central ray 42a and central center ray 40a pass though a common nodal point 41 of eye 10 located in lens 16 on optic axis 20. For convenience, it is often assumed in the art that the nodal point of the eye is located at the intersection of the plane of iris 14 and the optical axis 20, as indicated at 41a, but it is immaterial to this invention which nodal point is assumed. As internal angle β has been difficult to measure hitherto, the incident angle α of a peripheral ray will be used unless otherwise indicated. [The present invention now greatly facilitates precise measurement of internal peripheral angles β.]

Although the optic axis 20 of eye 10 is assumed to pass centrally through cornea 12 and fovea 26, the geometric axis (partially indicated at 43 of FIG. 1) of the substantially spherical sclera 22 is not exactly coincident with the optic axis 20 in human eyes so that the geometric center 44 of eye 10 does not lie exactly on optic axis 20. Moreover, the contour of the natural retina 18 is not exactly spherical and it may not be exactly rotationally symmetric about either the optic or the geometric axis. As already noted, for example, myopic retinas are more oblate than hyperopic retinas. The angle between a 'radius' drawn to a point r on an assumed spherical retina 18 from geometric center 44 and relative to geometric axis 43 is indicated as polar angle ∂. For the purpose of the present invention, the center 44 of retina curvature—whether assumed to be on axis 20 or slightly displaced therefrom, as shown at 44—can be regarded as another nodal point of the eye. Finally, it might be noted that the sagittal length of a normal eye—that is, the distance from anterior surface 35 of cornea 12 to fovea 26 along optic axis 20—is about 22.6 mm, the optic axis distance from anterior corneal surface 35 to nodal point 41 is about 5.6 mm, and the anterior chamber depth (ACD) from the posterior cornea surface 34 to nodal point 41a averages about 3 mm in humans. While the fovea has a diameter of about 2 mm, the retina covers about 70% of the interior of the spherical sclera of the posterior chamber, which is about 22 mm in diameter. Thus, the area of the retina is much greater than that indicated in FIG. 1, the peripheral area 18 being intended to indicate the area likely to be of interest for anti-myopia lens design.

FIGS. 2a-2e further illustrate the concept of retinal area with reference to an idealized basic model eye 10a. In these Figures elements that are common to natural eye 10 of FIG. 1 are indicated by the same reference numerals but with the addition of the suffix 'a'. It will be appreciated that the simulated cornea 12a can be a solid lens rather than a meniscus lens as shown, iris 14 can be a simple aperture disc and lens 16 can be an IOL under test. It is convenient to arrange model eye 10a so that its optic axis 20a is vertical and simulated cornea 12a is uppermost to allow a test contact lens 45 to be rested in correct alignment on the anterior surface of cornea 12a (as is known in the art) and it is convenient to construct the model eye so that the cornea, iris and lens are mounted in a replaceable 'front-end' module to allow, for example, simulation of old or young eyes and of various corneal profiles, different IOLs and some eye pathologies. Of course, an appropriately arranged test spectacle lens (not shown) can be substituted for test contact lens 45.

It is of interest to know where central and peripheral images of objects in the field of view of model eye 10a are brought to focus in relation to the measured or supposed location and contour of the retina 18a, whether normal or pathological. For example, referring to FIG. 1, for on-axis images it is desirable to determine the precise location of point f, fm, or fh and, in the case of off-axis images, it would be desirable to know the location of specific focal points such as p and ph as well as curvature of field contour cf in both the assisted and unassisted model eye. Furthermore, as the point of best focus can be determined by moving a detector or reflector backwards and forwards 'through-focus', a region before and behind each point is also involved. Thus, there is a substantially spherical-form cup-like retinal area 46 at the back of the model eye 10a in FIG. 2a that encompasses (i) the measured or assumed location and contour of a normal retina 18a, (ii) the measured or assumed locations and contours of abnormal retinas such as that of a myope 18m or that of a hyperope 18h indicated in broken lines, (iii) focusing errors and aberrations due to other optical components of model eye 10a, such as cornea 12a, iris 14a and lens or an IOL 16a, (iv) image shift, improvement or degradation caused by corrective lenses or simulated corneal molding, (v) location of specific focal points, such as those identified in FIG. 1, (vi) curvatures of field both for the assisted and unassisted model eye, and (vii) the small area or layer before and behind all these points and contours needed to permit through-focusing. Thus, considered most generally, the retinal area 46 can be regarded as a cup-like spherical-form shell as illustrated in the sectional diagram of FIG. 2a.

Figures 2A, 2B, 2D:
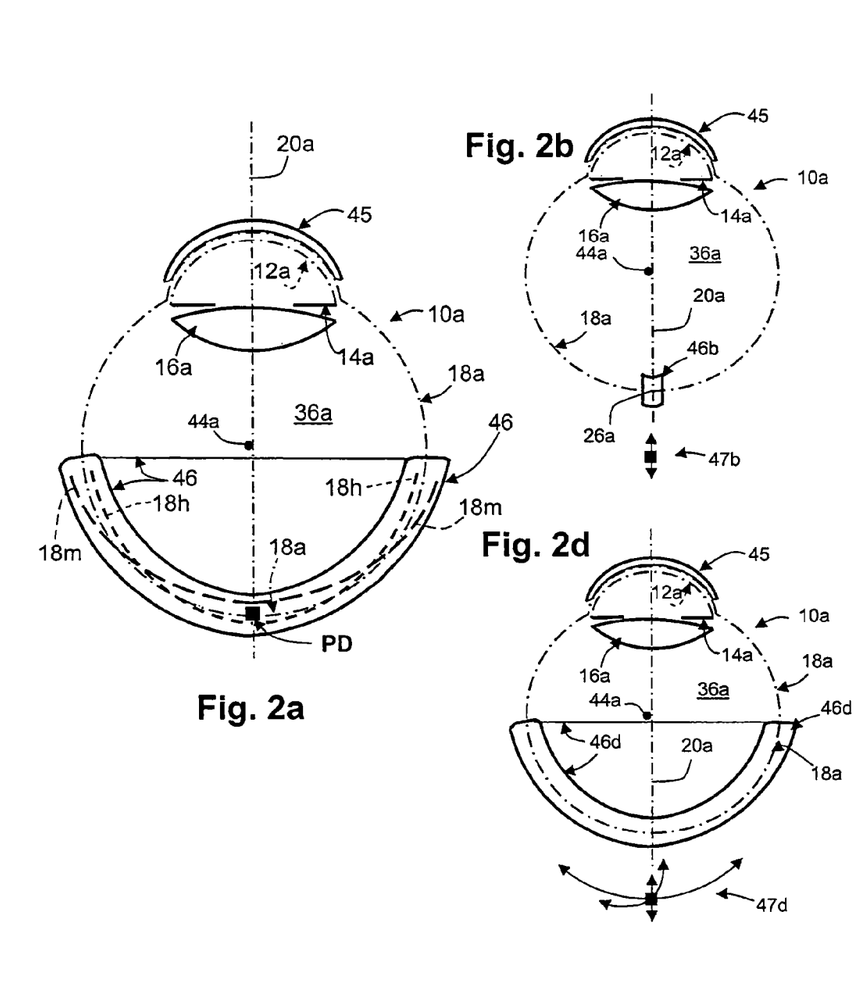
FIGS. 2a to 2d are elementary sectional diagrams illustrating aspects of idealized model eyes.

The present invention involves the use and movement of a—preferably small—photoactive device, generally indicated in FIG. 2a at 'PD', anywhere within retinal area 46. Device PD may in fact be moveable much more widely within 'posterior chamber' 36a of the natural eye, with or without the presence of liquid simulating the vitreous humor. Device PD preferably has a photoactive area that is similar in area to that of the fovea of a natural eye. Whether device PD is an array of photodector cells (such as a CCD or CMOS chip) or a photoreflector simulating the reflective properties of the natural retina, it is desirable that it face a nodal point (41 or 41a, FIG. 1) or be arranged tangential to the retinal area so as to face nodal point (center of curvature) 44a. A photoemitter, preferably a point source will normally be directed at the nodal points 41 and 41a so as to illuminate the back of lens 16a but this may be varied by the actuator means (to be described). A photodetector device can be used to assess the quality of a small portion of an image on a presumed or pre-determined retinal contour; a photoreflector can be used to calibrate refractometer or wavefront devices used to interrogate the natural eye; a narrow-beam photoemitter can be used to optically align components of model eye 10a during calibration or set-up; a point-source photoemitter can be used in a single-pass technique for characterizing the model eye front-end optics using a wavefront analyzer or the like. While movement of device PD within area 46 is important, it need not be confined thereto.

Figure 2C:
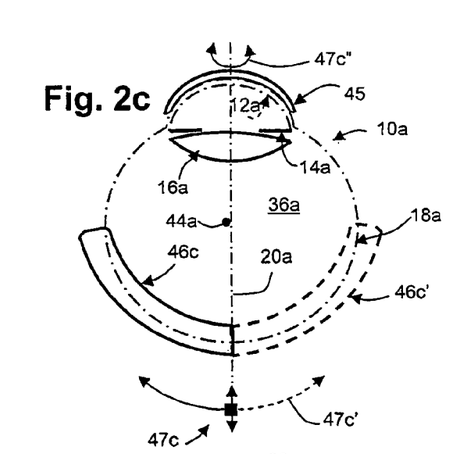
Figure 2E:
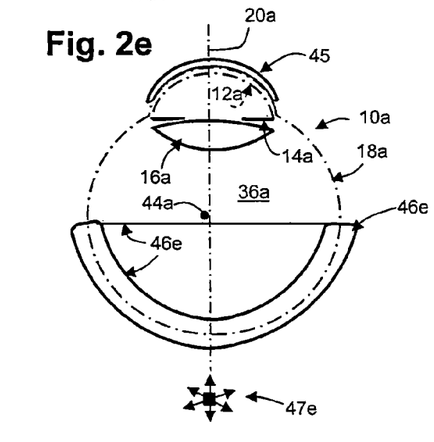

FIGS. 2b-2e illustrate a variety of retinal areas and various ways in which the device (not separately identified in these Figures for clarity) can be moved within them—and within posterior chamber 36a. The simplest is a short linear area 46b of FIG. 2b that extends axially in front of and behind fovea 26a. As indicated by arrows 47b in FIG. 2b, the device simply moves linearly and axially back and forth (to and fro)

through-focus at or near the location of the fovea of the simulated natural eye. Note from FIG. 2a that, in so doing, device will cut across a range of possible retinal contours of interest, such as 18a, 18m and 18h in FIG. 2a. While area 46b can thus be regarded as a narrow two dimensional line, it is preferably a short three dimensional cylinder of about fovea diameter centered on axis 20a because it is desirable that the device can be moved a little laterally from axis 20a to detect focal points within the fovea but not exactly on-axis. In FIG. 2c, retinal area 46c can be regarded as a thin arc or curved strip, with arrows 47c indicating both the to-and-fro through-focus radial motion and the circumferential motion in one quadrant or, optionally, in the opposing quadrant as well—as indicated by dashed lines at 46c' and arrow 47c'. If it is assumed that the retinal contours of interest are rotationally symmetric about axis 20a (but not necessarily spherical), then the data generated by the device in just a single quadrant can be extrapolated to represent the entire 3-D cup-like retinal area 46 of FIG. 2a. Asymmetries in test lenses and corneas will generally be accommodated by incrementally rotating a front-end module (containing the model cornea, iris and lens or IOL) of the model eye about the optical axis and making a scan of the retinal area, or along a retinal contour of interest, at each increment. Arrows 47c" are intended to illustrate such a rotation.

The retinal areas 46d and 46e (FIGS. 2d and 2e, respectively) are, however, fully three dimensional curved shells as in FIG. 2a and make no assumptions about rotational symmetry. The cluster of arrows 47d (FIG. 2d) indicate that the device can be moved to-and-fro (for through-focus) and arcuately in any direction for positioning anywhere within area 46d. And, although the device of FIG. 2e can also be positioned anywhere within retinal area 46e having essentially the same geometry, it is assumed to be mounted on a universal robotic arm capable of moving it directly to any set of Cartesian (or polar) coordinates within the three-dimensional retinal area 46e—and, optionally, much more widely within posterior chamber 36a outside area 46e. Cluster of arrows 47e are intended to indicate this.

Since, in any of the retinal areas (46b-46e) discussed above, movement of the photoactive device is preferably by means of a computer-controlled actuator, it will be appreciated that both the boundaries of the retinal area and particular retinal contours therein (eg, 18a, 18m and 18h in FIG. 2a) may not be tangible physical entities identifiable by inspection of a physical model eye.

We have found it most cost-effective to implement the single or two quadrant planar arcuate retinal area 46c/46c' of FIG. 2c for the purpose of evaluating retina shapes, contact lenses, spectacle lenses and/or IOLs. As indicated above, non-rotationally symmetrical retinal contours can be accommodated by using a succession of contour sections and a succession of scans on them. An asymmetric contact or spectacle lens can be evaluated by incrementally rotating it about the optic axis and making successive scans with the photoactive device. An asymmetric cornea or IOL can be evaluated by incrementally rotating a front-end module (within which it is incorporated) about the optical axis and making a scan at each increment. Examples of model eyes and model eye systems using the one or two quadrant retinal area of FIG. 2c are described with reference to FIGS. 3-6.

Figure 3:
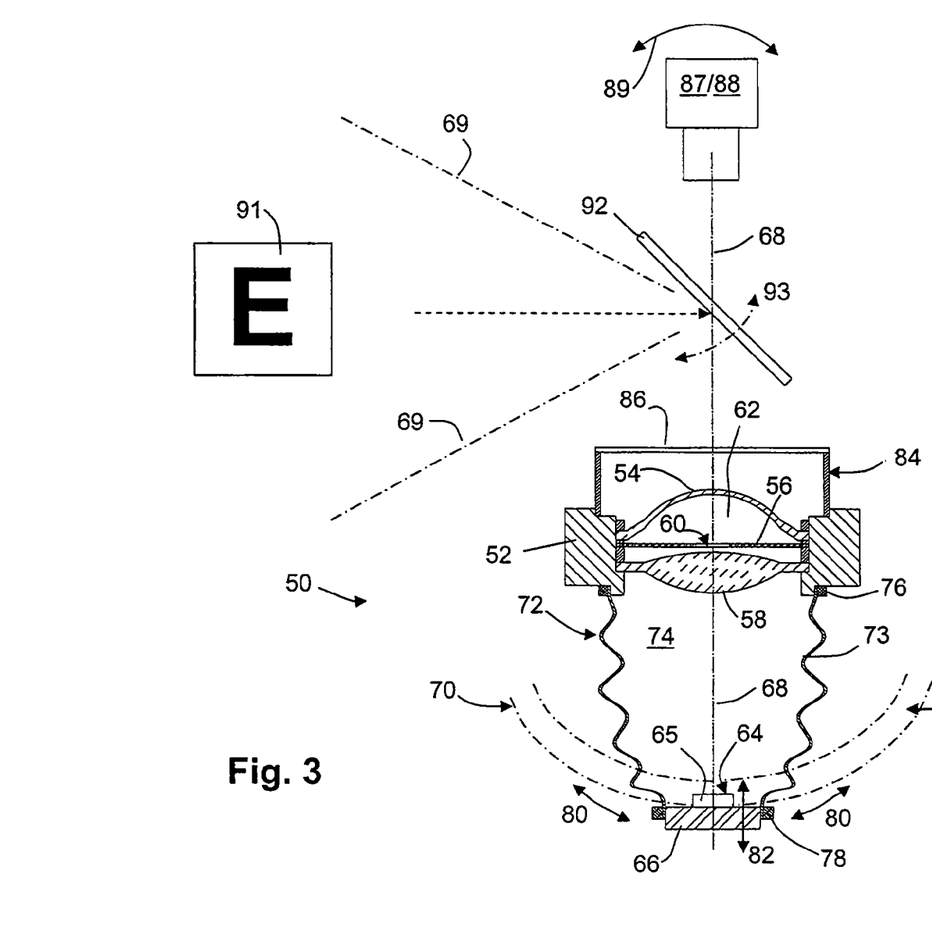
FIG. 3 is a diagrammatic sectional elevation of a physical model eye or system that forms the first example of the application of this invention.

Referring to FIG. 3, the physical model eye 50 of this example is shown in sectional elevation to indicate its basic components. These are a mounting ring 52 for holding the simulated cornea 54, iris 56 and model lens or IOL 58. In this case, lens 58 is formed of solid glass or plastic to have a power typical of a natural human lens, iris 56 can be a simple replaceable aperture plate having a central hole or pupil 60 of fixed size, and cornea 54 is a meniscus lens accurately machined or molded to have realistic anterior and posterior contours. The anterior chamber 62 can be filled with a liquid (not shown) to simulate the aqueous humor. In this case, the photoactive device (generally indicated at 64) comprises a photodetector array 65 mounted on a base 66 which, as shown in FIG. 3, happens to be positioned on optic axis 68 of model eye 50.

In this example, cornea 54, pupil 60 and lens 58 are substantially life size, the distance between them approximates those between the corresponding elements of a natural human eye and the anterior chamber depth (ACD FIG. 1) and the saggital length of model eye 50 approximate the corresponding dimensions of a natural eye. Model eye 50 has a field of view, diagrammatically indicated by dot-dash lines 69, that is substantially the same as that of the natural human eye. In FIG. 3 the curvature of the retinal area 70 has been distorted for clarity. A posterior enclosure 72 is formed by a tubular, flexible and bellows-like bladder 73 that encloses much of the normal posterior chamber 74 of an equivalent natural eye (10, FIG. 1), bladder 73 being sealed at its top 76 to mounting ring 52 and at its bottom 78 to device base 66. As indicated by arrows 80, device 64, base 66 and bottom 78 of bladder 73 are conjointly moveable arcuately in such a way that device 64 travels within retinal area 70 while facing toward the center of curvature (not shown) of area 70. Arrows 82 indicate that device 64 is also moveable to and from lens 58 and cornea 54 (and/or a nodal point of eye 50) to determine the radial location where best focus is achieved, or to position device 64 on a predetermined retinal contour (not shown) within retinal area 70 and to assess the resultant image quality.

As is known in the art, a cover 84 with a transparent top 86 may be arranged over cornea 54 to reduce evaporation of tear solutions (not shown) when a contact lens (not shown) is placed on cornea 54 or when the optical effects of different tear solutions are being investigated.

In this example, a camera unit 87 is arranged above model eye 50 on axis 68 so as to record an image of a test contact lens (not shown in FIG. 3, but illustrated in FIG. 6) when placed onto cornea 54. From this image, fit, centration and meridional orientation of the test contact lens can be determined, confirmed and/or recorded. This is of particular advantage where test lenses have significant power variations across their optical zones, such as concentric and translating bifocal, multifocal, 'anti-myopia' and toric contact lenses.

A method of presenting a test image to eye 50 is to use a test object or scene within field of view 69, as illustrated by illuminated wall chart 91 of the type commonly used for testing the visual acuity of the human eye, but other test objects may be arranged at different distances and angles within field of view 69 instead of or in addition to chart 91. Light reflected from chart 91 is directed by a mirror or beam-splitter 92 axially into eye 50. If desired, mirror or beam-splitter 92 can be rotated as indicated by arrows 93 to vary the field of view along with the test objects therein. The setup shown in FIG. 3 is of particular value for the assessment of bifocal contact lenses using near and distant test objects in the field of view. [Mirror or beam-splitter 92 would normally be removed during alignment or calibration using camera unit 87.]

Figure 4:
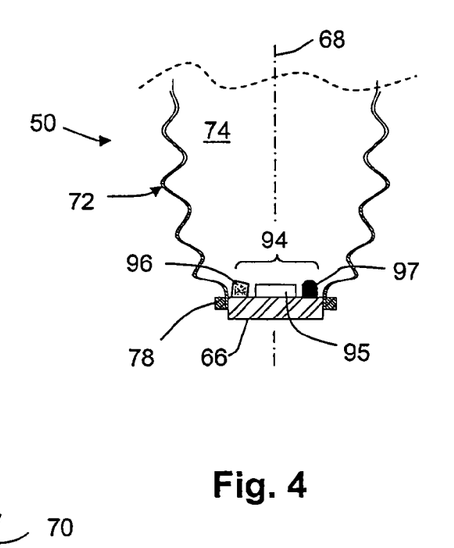
FIG. 4 is a diagrammatic sectional elevation of a portion of the model eye or system shown in FIG. 3 illustrating an alternative photoactive device.

FIG. 4 reproduces the lower end of posterior enclosure 72 of FIG. 3 to illustrate a multi-functional photoactive device 94 that may be used as an alternative to the device 64 of FIG. 3. In this variant, device 94 comprises a photodetector array 95, a reflector 96 and a solid-state point-source light emitter 97. As the distances between these three photoactive devices are known, any one can be moved into line with optic axis 68 and zeroed there so that it can be moved to any desired location within retinal area 70 with precision. Of course, light source 97 will only be activated and moved to position when selected and data from array 95 will only be collected when it has been selected and moved to position. Likewise, reflector 96 will only be moved to position when it is to be used with an external optical instrument such as a refractometer or wavefront analyzer 88, which when substituted for camera unit 87, directs an interrogating beam into the eye and compares light reflected or backscattered from reflector 96 with the interrogating beam. As known in the prior art such instruments can be angled with respect to optical axis 68 as indicated by arrows 89 in FIG. 3.

In another arrangement where photodetector array 95 is activated and appropriately positioned, the external optical instrument 88 can be a point light source that directs light into the model eye so that higher order aberrations of the front-end of the eye (with or without correctional lenses in place) can be determined using data generated by array 95. This has the advantage of being a single-pass technique instead of the double-pass techniques employed by a refractometer and wavefront analyzer.

Figure 5:
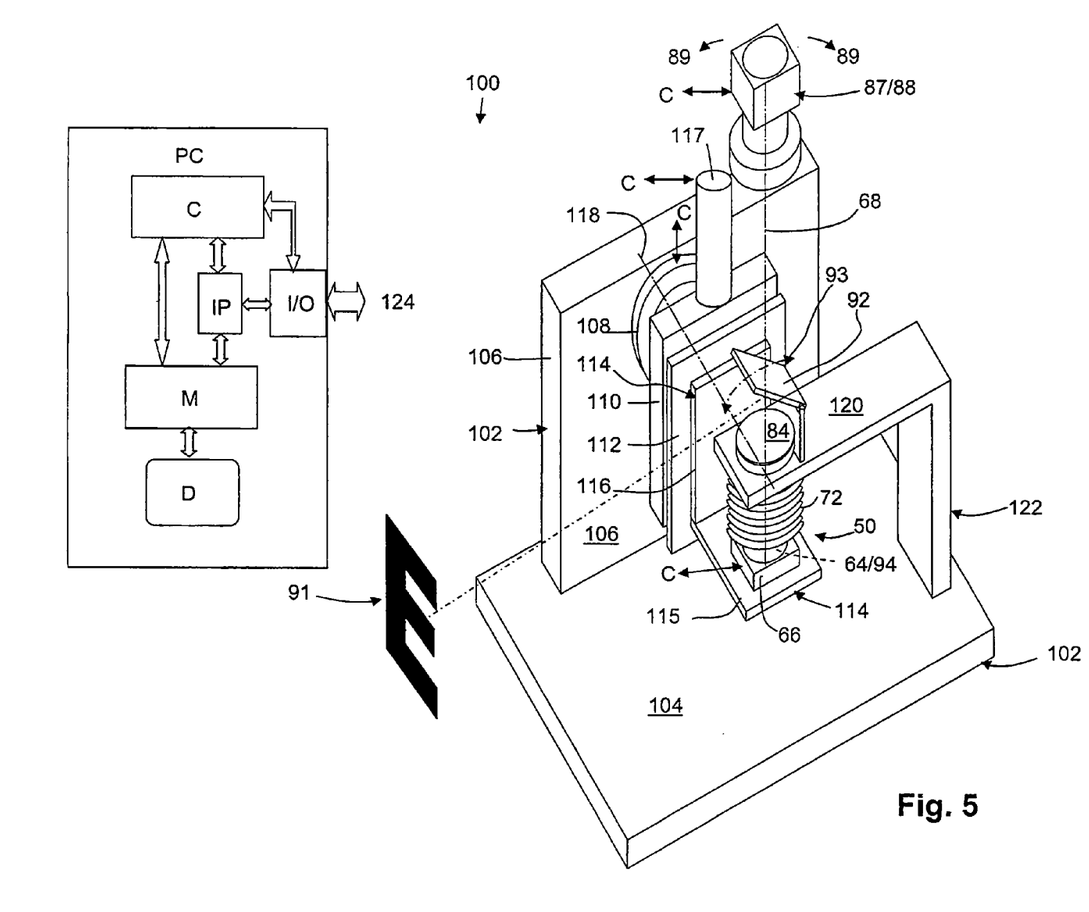
FIG. 5 is a diagrammatic perspective of an optical instrument comprising another example of a model eye system.

FIG. 5 illustrates model-eye system 100 incorporating model eye 50, along with the camera/alignment unit 87 and beam-splitter 92 of FIG. 3. System 100 preferably includes a computer-processor PC comprising a controller C, an image processor IP, a memory M, a display D, and an input-output interface I/O by which computer-processor PC is connected to the mechanical components of model eye system 100. Controller C is connected via interface I/O to actuators (to be described) that move device 64/69. Memory M stores relevant control programs and reference retinal contours as well as image and positional data generated by image processor IP. The stored control programs and retinal contours are accessed by controller C to drive the actuators via interface I/O and the image and positional data generated (returned via interface I/O) are analyzed and manipulated by image processor IP before being stored in memory M and/or displayed by display D. Computer-processor PC is thus able to monitor and control all important functions of system 100, including the operation of camera unit 87 or instrument 88, if desired.

System 100 has a frame 102 comprising a horizontal base 104 and a vertical back 106 rigidly fixed to base 104. A rotary actuator 108 is mounted on back 106 to rotatably support a slider base 110 that in turn carries a slider 112 on which an L-shape support arm 114 is mounted, arm 114 having a horizontal portion 115 that carries base 66 of the photoactive device 64/94 (shown with a dashed lead-line as it is not visible in FIG. 5) and a vertical portion 116 that is attached to slider 112. Slider 112 is moved to-and-fro on rotatable slider base 110 by a linear actuator 117 mounted on slider base 110. Rotary actuator 108 is arranged so that its axis of rotation 118 is horizontal and passes through a nodal point (41,41a or 44 FIG. 1) of the model eye 50, irrespective of the vertical location of device base 66 relative to axis 118 set by linear actuator 117. Mounting ring 52 (FIG. 3) of model eye 50 is not visible in FIG. 5 being located within the horizontal arm 120 of a bracket 122 that is fixed to frame base 102, the top of ring 52 and the cornea of model eye 50 being covered by cover 84. Mirror 92 is mounted on arm 120 of bracket 122 above cover 84.

Double-headed arrows C near actuators 108 and 117, photoactive device base 66 and large double-headed arrow 124 near interface I/O indicate two-way connections to and from computer-processor PC. It will be appreciated that computer-processor PC can be readily programmed to control actuators 108 and 117 to swing support arm 114 about axis 118 and place the photoactive device (64/94) at a predetermined position within the retinal area (70, FIG. 3) of model eye 50, and to then control linear actuator 117 to move the device to-and-fro on slider 112 for through-focusing. If the retinal area 70 is assumed to be rotationally symmetric about optic axis 68, the arcuate path will be sufficient to define the entire three-dimensional retinal area 70. If it is further assumed that the cornea and lens (54 & 58, FIG. 3) and any contact lens placed on the cornea are rotationally symmetric about optic axis 68, then this two-dimensional path will be sufficient to characterize the image quality within the three-dimensional spherical-form retinal area and, if desired, with respect to a non-rotationally symmetric three-dimensional retinal contour stored in memory M.

The portion of the retinal area 70 examined using system 100 will depend upon the interests of the investigator, as already indicated in the discussion of FIGS. 2a-2d. Those interested only in the design and performance of multi-focal contact lenses or IOLs for central vision may have little interest in the quality of the peripheral image at incident peripheral angles greater than about 15 degrees. On the other hand those concerned with the investigation of progressive myopia and with the design and use of anti-myopia lenses will be keenly interested in the nature of the peripheral image for incident or solid peripheral angles out to least 30°, as well as in the quality of central vision. It will be most useful for the latter investigators to be able to plot the curvature of field for a given model eye and artificial lens combination well into the peripheral retina and to compare such plots with pre-recorded measurements of retinal topography or with reference to specific retinal contours generated by measurement, theory or computation and stored as reference data in memory M. Many alternative retinal contours exhibiting various pathologies or abnormalities of natural eyes, such as decentration, asymmetry, eye length and the like, can be generated and stored for comparison or use in this way.

Although the field of movement of device 64/94 in the model eye system or instrument 100 is essentially a planar arc that extends either side of optical axis 68 in a single meridian, this does not mean that only rotationally symmetric three dimensional retinal contours can be simulated. As described with reference to FIGS. 2a-2d, the coordinates of any three-dimensional asymmetric retinal contour can be stored in memory M and used (by computer-processor PC) to generate a series of contour sections at incremental meridia to guide or reference the movement of device 64/94 in repeated scanning movements. Similarly, system 100 is not confined to testing rotationally symmetric contact lenses, spectacle lenses or IOLs, if they can be incrementally rotated around optical axis 68. First, device 64/94 can be moved along the predetermined retinal contour or path on both sides of axis 68 so that any affect of asymmetry in the test lens in the meridian of movement will be detected and quantified. Second, the test lens can be incrementally rotated with respect to model eye 50 and device moved over its arcuate path for each increment. But this may laborious, prone to error in the alignment of the test lens. Furthermore, to quantify the effects of asymmetry in, say, a test cornea or IOL, it will be necessary to disassemble and reassemble the front-end of the model eye for incremental rotation of the component concerned. However, a variety of modifications to system 100 can be made that will more conveniently account for asymmetry in the cornea or IOL and, in the event that these are rotationally symmetrical, more conveniently account for asymmetry in test corrective spectacle or contact lenses.

In accordance with a variant of the system of FIG. 5, the entire model eye (50) can be rotatably mounted in bracket 122 and turned about optic axis 68 by a suitable rotary actuator (not shown) controlled by computer processor PC. A preferred alternative is to rotate only the mounting ring 52 in bracket 122 and to provide a water-tight rotary joint at the top 76 or bottom 78 of enclosure 72 (FIG. 3). Most preferable, however, is the use of replaceable and rotatable front-end modules as illustrate in FIG. 6, which give the model eye system 100 even greater utility.

Figure 6:
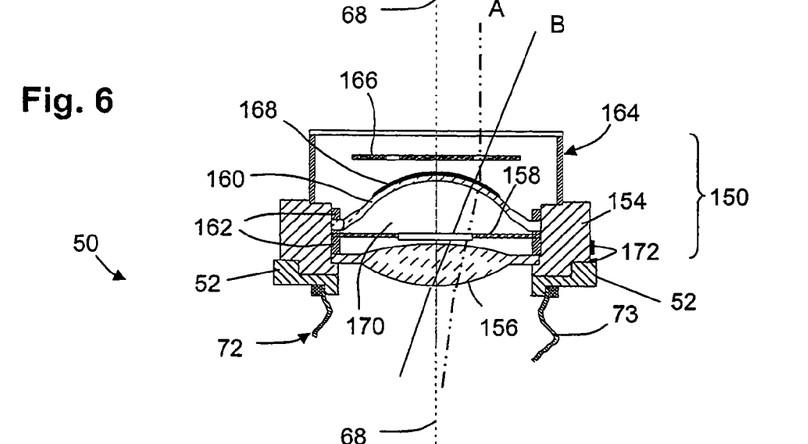
FIG. 6 is a diagrammatic sectional elevation of a replaceable and rotatable 'front end' module of a model eye similar to that of FIG. 3 and also illustrates the use of masks for confining incident radiation to specific zones of the cornea (and corresponding retinal areas), FIGS. 6a, 6b and 6c being plan views of three such masks.

Referring to FIG. 6, mounting ring 52 of model eye 50 and/or system 100 is modified by the formation of an annular recess to take a replaceable front-end module 150, suitable arrangements being made to ensure that the joint between the bottom of module 150 and ring 52 is fluid-tight. Module 150 basically comprises a lens tube 154 within which a model lens or test IOL 156, iris aperture plate 158 and cornea 160 are mounted by spacer rings 162. Module 150 may also conveniently include a protective cover 164 (having the same function as cover 84 described with reference to FIG. 3) and a mask disc 166 that is preferably mounted within cover 164 (as shown in FIG. 6) but can be simply placed on top of it. [The function of mask disc 166 will be described below.] A contact lens 168 for evaluation is shown in place on cornea 160. Such modules can be conveniently pre-assembled at a location remote from the rest of model eye 50 and/or system 100 so that all optical components are correctly aligned and spaced. If desired, the anterior chamber 170 between lens 156 and cornea 160 can be pre-filled with liquid (not shown) representing the aqueous humor of the natural eye. Module 150 can be quickly located in and removed from mounting ring 52 so that, for example, iris plate 158 or mask 166 can be replaced and the module returned for a further set of measurements using system 100. Furthermore, module 150 can be rotated around optical axis 68 in a precise and convenient way using a degree scale marked on the outside of lens tube 154 and a datum mark on mounting ring 52, these marks being jointly indicated at 172. This enables precise and repeatable rotational orientation of module 150 and test lens 168 in model eye 50 and system 100, which is important where lens 168 is asymmetric or decentered.

However, in addition to the advantage of being able to conveniently assemble or change the optical components of module 150 at a location remote from the rest of system 100, a set of quickly replaceable front-end modules can greatly speed up the evaluation of test lens 168. Such a set may comprise, for example, a number of pre-assembled and substantially identical modules that differ from one another only in pupil size determined by the use of different iris plates 158 in different modules so that test lens 168 can be quickly evaluated for a range of pupil sizes without the need to disassemble any module. Similarly, where lens 156 is an IOL that is under evaluation, a set of front-end modules can be made up using identical test IOLs but with varying alignment errors, as well as different pupil sizes if desired. Modules representative of various pathologies can also be made up in advance for evaluating corrective spectacle lenses, contact lenses or cornea shapes. Examples of such 'pathological modules' are those with presbyotic lens shapes, keratoconus or keratoglobus cornea shapes and those with ACDs indicative of glaucoma.

Figure 6A:
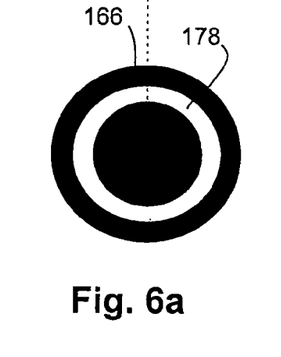
Figure 6B:
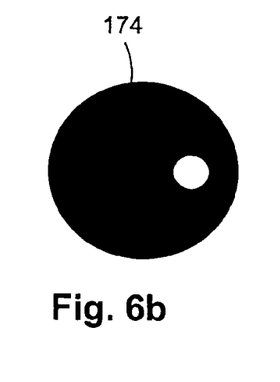
Figure 6C:
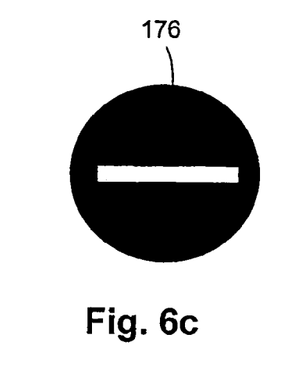

The use of mask 166 (shown in plan view in FIG. 6a) and alternative masks 174 (FIG. 6b) and 176 (FIG. 6c) to select incident rays or beams for the testing of a corrective lens or for evaluating the image at particular positions on a retinal contour, will now be described. Mask 166 is a ring mask with a peripheral transparent ring 178 which allows only a thin circular ring of cornea 160 and IOL 156 to be illuminated. As shown in FIG. 6, selected incident paraxial rays A and peripheral off-axis rays B pass through mask 166 so as to generate images in the central and peripheral retinal areas (respectively) for analysis. FIG. 6a is a plan view of the ring mask 166 while FIG. 6b shows alternative spot-mask 174 that also permits rays A and B to pass into model eye system 50 but only in one meridian and quadrant. Alternative slot mask 176 is shown in FIG. 6c which is useful for confining incident light to the same meridian or quadrant as swept by device 64 (FIG. 3).

It will be appreciated that the modifications to allow rotation of the front-end of a model eye described above enable the front-end of the model eye to be rotated about optic axis 68 in a stepwise manner and that, at each rotational step, device 64 is scanned from position to position along its arc so that, at each position, the detected image portion and/or the location of best-focus can be captured.

Those skilled in the art will appreciate that many other modifications and alternative embodiments can be made without departing from the nature and scope of the invention as outlined above and as defined in the following claims.

The invention claimed is:

1. A model eye system having an anterior cornea surface and a posterior retinal area where images of external objects within a field of view can be brought to focus, the system having a longitudinal optical axis that passes through both the anterior cornea surface and the retinal area, wherein:
   a photoactive device is movable both axially and laterally within the retinal area and is adapted to detect or reflect a portion of an image formed in the retinal area.

2. The model eye system according to claim 1 wherein:
   said device is supported by actuator means for both axial and lateral movement to position the device within the retinal area, and
   said device is a photodetector adapted to detect said image portion and to generate an output representative of the detected image portion at each position of the device within the retinal area.

3. The model eye system according to claim 2, wherein:
   image processor means is connected to receive said output of the device and to output data representative of the detected image portion at said each position of the device within the retinal area.

4. The model eye system according to claim 3, wherein:
   said actuator means is adapted, at said each position, to reciprocate the device through a plurality of locations, and
   said image processor means is adapted to determine location of best-focus and to output best-focus data indicative thereof.

5. The model eye system according to claim 3, wherein:
   controller means is connected to said actuator means and is adapted to control the actuator means to move the device to successive positions within the retinal area,
   said image processor means is adapted to compute a curvature of focal field from the location of best-focus for said successive positions of the device within the retinal field and to output data indicative of said curvature of field.

6. The model eye system according to claim 3, wherein:
   memory means is provided for the storage of the spatial coordinates of a retinal contour located within the retinal area,
   controller means is connected to said actuator means and to said memory means, said controller means is adapted to control the actuator means to move the device within the retinal area to a predetermined position having spatial coordinates of a point on said retinal contour, and said image processor means is adapted to output data representative of the detected image portion at said predetermined position on the retinal contour.

7. A model eye system having an anterior cornea surface and a posterior retinal area where images of external objects within a field of view can be brought to focus, the system having a longitudinal optical axis that passes through both the anterior cornea surface and the retinal area, wherein:
- a photoactive device is movable both axially and laterally within the retinal area and is adapted to detect or reflect a portion of an image formed in the retinal area, and
- said device is supported by actuator means for both axial and lateral movement to position the device within the retinal area, and
- said device is a photodetector adapted to detect said image portion and to generate an output representative of the detected image portion at each position of the device within the retinal area, and wherein:
- said actuator means comprises a rotary actuator adapted to move the device in an arcuate manner about an axis of rotation that substantially intersects the optical axis at or near a nodal point of the model eye system.

8. The model eye system according to claim 7, wherein:
the actuator means comprises a linear actuator adapted to reciprocate the device across the retinal area toward and away from the cornea surface,
said linear actuator is supported by said rotary actuator for arcuate movement with the device about said axis of rotation, and
said rotary actuator and said linear actuator jointly enable said lateral and axial movement of said device within the retinal area.

9. The model eye system according to claim 1, wherein:
a posterior enclosure encloses at least a portion of the retinal area,
said enclosure is adapted to hold liquid optically representative of the vitreous humor of the natural eye,
said enclosure has a posterior end within which said device is mounted so that the device will be immersed within said liquid when such liquid is held by the enclosure, and
said enclosure has a flexible wall allowing movement of the device within the retinal area.

10. The model eye system according to claim 2, wherein:
said cornea, iris and lens of said front-end module are arranged on a common axis, and
said module is adapted for mounting in the model eye system coaxially with the optical axis thereof and so that the module can be rotated about the optical axis.

11. The model eye system according claim 1, wherein the device has a photoactive area that approximates the area of the fovea of a natural eye.

12. The model eye system according to claim 1, wherein:
the device has a photoactive area that is small relative to the retinal area.

13. The model eye system according to claim 1, wherein:
the device has a photoactive area that has a lateral dimension of between about 1 mm and about 4 mm in length.

14. The model eye system according to claim 2, wherein said photodetector comprises a two-dimensional array of color-sensors.

15. The model eye system according to claim 1, wherein the device includes a photoreflector arranged to reflect an image portion toward the cornea surface to enable detection of said image portion by an optical instrument located in front of the cornea surface.

16. The model eye system according to claim 1, wherein the device includes a point light source arranged, when energized, to direct light toward the cornea surface to enable detection by an optical instrument located in front of the cornea surface.

17. A model eye system having an anterior cornea surface and a posterior retinal area where images of external objects within a field of view can be brought to focus, the system having a longitudinal optical axis that passes through both the anterior cornea surface and the retinal area, wherein:
- a photoactive device is movable both axially and laterally within the retinal area and is adapted to detect or reflect a portion of an image formed in the retinal area; and wherein said retinal area comprises a shape selected from the group consisting of:
- substantially linear and extending along the optic axis;
- a substantially planar arc, having a concave anterior side and extending laterally and forwardly from the optical axis; and
- a substantially spherical three-dimensional cup-like shell substantially centered on the optical axis.

18. An optically realistic model eye having an optical axis and including:
- an anterior replaceable module comprising a model cornea, model iris and model lens rotatably mounted for rotation about said axis, said module being representative of an emmetropic or pathological natural eye,
- an enclosure located posterior to said module and adapted to enclose a retinal area within which an image of an external object is brought to focus by said module, and
- a photoactive device movable within said enclosure and retinal area and adapted to detect or reflect a portion of the image for inspection, processing or analysis.

19. The model eye system according to claim 1, which has an optically realistic lens, cornea and iris.

20. The model eye system according to claim 19 in which a retinal surface of the model eye is approximated by lateral and axial movement of the photoactive device.

21. The model eye system according to claim 1 which is substantially life-size, and which has a field of view which is similar to that of the natural eye.

22. The model eye system according to claim 20 which is substantially life-size, and which has a field of view which is similar to that of the natural eye.

* * * * *